United States Patent [19]

Arai et al.

[11] Patent Number: 5,013,527

[45] Date of Patent: May 7, 1991

[54] INTEGRAL MULTILAYER ANALYTICAL ELEMENT FOR ANALYSIS OF ALBUMIN

[75] Inventors: Fuminori Arai; Takeshi Takayama, both of Saitama, Japan

[73] Assignee: Fuji Photo Film Co., Ltd., Kanagawa, Japan

[21] Appl. No.: 234,465

[22] Filed: Aug. 19, 1988

[30] Foreign Application Priority Data

Aug. 20, 1987 [JP] Japan .................................. 62-207259

[51] Int. Cl.$^5$ ............................................. G01N 21/00
[52] U.S. Cl. ........................................ 422/56; 422/57; 422/58; 436/71
[58] Field of Search ..................................... 422/56–58; 436/71, 85, 166, 178

[56] References Cited

U.S. PATENT DOCUMENTS

| | | | |
|---|---|---|---|
| 3,485,587 | 12/1969 | Keston | 436/88 |
| 3,533,749 | 9/1970 | Kleinman | 436/88 |
| 3,672,845 | 6/1972 | Verbeck | 422/57 |
| 3,992,158 | 11/1976 | Przybylowicz et al. | 436/808 |
| 4,042,335 | 8/1977 | Clement | 422/56 |
| 4,333,733 | 6/1982 | Sanford et al. | 422/56 |

FOREIGN PATENT DOCUMENTS 62-243364 10/1986 Japan .
62-24150 2/1987 Japan .
62-27664 2/1987 Japan .

*Primary Examiner*—David L. Lacey
*Assistant Examiner*—Lyle Alfandary-Alexander
*Attorney, Agent, or Firm*—McAulay Fisher Nissen Goldberg & Kiel

[57] ABSTRACT

In an integral multilayer analytical element for the analysis of albumin where at least one hydrophilic polymer binder layer and a porous spreading layer containing an indicator capable of binding to albumin to produce a color change are integrally superposed on a light-transmissive water-impermeable support in this order, the improvement comprising said indicator being dispersed in a hydrophilic polymer or a mixture of a hydrophilic polymer and a hydrophobic polymer and a pH buffer being incorporated into the spreading layer.

In the analytical element of the invention, the error caused by the competitive inhibition by globulin can be removed by making to produce the color due to the bonding between albumin and indicator relatively much in the support side (lower side) portion of the porous spreading layer and by making to produce the color due to the bonding between globulin or other proteins and indicator relatively much in the outer surface side (opposite side to the support, upper side) portion of the porous spreading layer.

7 Claims, No Drawings

INTEGRAL MULTILAYER ANALYTICAL ELEMENT FOR ANALYSIS OF ALBUMIN

BACKGROUND OF THE INVENTION

1. Field of the Invention

This invention relates to a dry-type analytical element for the analysis of albumin, and more particularly, relates to an integral multilayer analytical element being dry operative for the quantitative analysis of albumin in biological body fluids, such as blood, cerebrospinal fluid, saliva, lymph and urine.

2. Background of the Invention

It is known that tha albumin in biological body fluids, such as blood, cerebrospinal fluid, saliva, lymph and urine, can be measured or determined by using a buffered Bromocresol Green (BCG) solution or a test piece disclosed in U.S. Pat. Nos. 3 533 749 or 3 485 587 according to the principle of colorimetry. BCG is one of acid-base indicator belonging to sulfonphthalein dyes.

Acid base indicators such as BCG are not specific for albumin. The globulin, transferrin and other proteins existing in human body fluid competes with albumin to bind to acid-base indicator, and give an error in the measured value. The above competitive inhibition is particularly remarkable in a low concentration of albumin. The total protein concentrations of human sera are usually in the range of about 6 to 8 g/dl. Globulin concentration in the total protein is usually about 2.9 g/dl, and the remainder is mainly albumin. The competitive inhibition appears in the above albumin concentration.

DESCRIPTION OF THE PRIOR ART

A dry type integral multilayer analytical element where the competitive inhibition is decreased is disclosed in U.S. Pat. No. 4,333,733. This analytical element is composed of a porous spreading layer (reacting layer ; reaction zone), a reagent layer containing BCG (reagent zone), a buffer and a nonprotein polymer binder dispersed therin and a transparent support superposed in this order. When a human serum sample is spotted onto the spreading layer, moisture is supplied to the reagent layer through the spreading layer. Both layers become wet and in contact with each other, and BCG in the reagent layer diffuses and migrates into the spreading layer. Then, BCG preferentially reacts with albumin, and change into the color characteristic of BCG albumin bond. The color concentration after the color change is measured, and the albumin content is calculated based upon the principle of colorimetry. However, the inventors have foud that, when the measuring time was elongated to such as about 3 to 7 munutes, the error which cannot be neglected appeared due to the competitive inhibition by interference components such as globulin.

Another dry-type integral multilayer analytical element for the analysis of albumin where the competitive inhibition by globulin is decreased is disclosed in Japanese Patent KOKAI Nos. 243364/1986 and 137564/1987. This analytical element is composed of a porous spreading layer containing BCG or another indicator incorporated by impregration (reagent containing spreading layer), a hydrophilic nonprotein polymer binder layer containing a pH buffer (PH buffer-containing water absorption layer) and a transparent support superposed in this order. A modified analytical element of this element is disclosed in Japanese Patent KOKAI No. 27664/1987. In the modified analytical element, a dicarboxylic acid such as glutaric acid, adipic acid, pimelic acid ro their derivatives is incorporated into the pH buffer-containing water absorption layer as the pH buffer. However, it has also been found that the competitive inhibition of globulin still appeared in these analytical elements.

Another dry-type integral multilayer analytical element for the analysis of albumin where the competitive inhibition by globulin is further decreased is disclosed in Japanese Patent KOKAI No. 24150/1987. This analytical element is composed of a fibrous porous spreading layer containing an indicator such as BCG immobilized with a reactive polymer (reagent spreading layer), a hydrophilic nonprotein polymer binder layer containing a pH buffer (pH buffer containing water absorption layer) and a transparent support superposed in this order. However, it has been found that the above analytical element has the problems of slow coloring rate and low sensitivity due to the immobilization of the indicator.

SUMMARY OF THE INVENTION

An object of the invention is to provide a dry-type integral multilayer analytical element for the analysis of albumin capable of decreasing the error caused by the competitive inhibition by globulin and other proteins.

Another object of the invention is to provide a dry-type integral multilayer analytical element for the analysis of albumin having a simple layer composition, easily producible, and capable of decreasing the error caused by the competitive inhibition by globulin and other proteins.

Another object of the invention is to provide a dry-type integral multilayer analytical element for the analysis of albumin capable of decreasing the error caused by the competitive inhibition by globulin and other proteins and capable of measuring albumin selectively and accurately, by making to produce the color due to the bonding between albumin and indicator relatively much in the support side (lower side) portion of the porous spreading layer and by making to produce the color due to the bonding between globulin or other proteins and indicator relatively much in the outer surface side (opposite side to the support, upper side) portion of the porous spreading layer.

The present invention provides a dry type integral multilayer analytical element for the analysis of albumin which has been achieved such objects. The analytical element of the invention has at least one hydrophilic polymer binder layer and a porous spreading layer containing an indicator capable of binding to albumin to produce a color change, integrally superposed on a light-transmissive water-impermeable support in this order, and it is characterized by that the above indicator is dispersed in a hydrophilic polimer or a mixture of a hydrophilic polymer and a hydrophobic polymer and that a pH buffer is incorporated into the spreading layer.

DETAILED DESCRIPTION OF THE INVENTION

The porous spreading layer used for the porous spreading layer containing an indicator (reagent-containing spreading layer) may be spreading layers of woven fabric disclosed in U.S. Pat. No. 4,292,272 and GB 2,087,074A, such as plain weaves including broad cloth and poplin, spreading layers of knitted fabric disclosed in EP 0,162,302A such as tricot fabric, double tricot fabric and milanese fabric, spreading layers composed of a paper containing fibrous pulp of an organic polymer disclosed in Japanese Patent KOKAI No. 148250/1982, membrane filters (blushed polymer layer) disclosed in U.S. Pat. No. 3,992,158, continuous microspaces-containing porous layers where polymer particulates, glass particulates or diatomaceous earth are dispersed in a hydrophilic polymer binder, continous microspaces-containing porous layers where polymer particulates, glass particulates, etc. are joined so as to contact with each other at a point by using a polymer adhesive which does not swell in water (three-dimensional lattice structure layer) disclosed in U.S. Pat. No. 4,258,001. Preferable spreading layers include fibrous spreading layres represented by woven fabric spreading layers and knitted fabric spreading layers in view of easy incorporation of the hydrophilic polymer containing the indicator dispersed therein.

Preferable indicators capable of binding to albumin to produce a color change include the acid-base indicator dyes indicating protein error described in I. M. Kolthoff, "Acid-Base Indicators", MacMillan, 1937, pp 350–353. Examples of such an acid-base indicator are sulfonphthalein indicator dyes such as Bromocresol Green, Bromocresol Purple, Bromothymol Blue, Bromophenol Blue, Chlorsphenol Red, Phenol Red, Cresol Red, Thymol Blue and Cresolphthalein, indigoid dyes such as Indigo Carmine, and azo dye indicators such as Methyl Red and Methyl Orange. Among them, Bromocresol Green (BCG) and Bromocresol Purple (BCP) are particularly preferable. A suitable content of the acid-base indicator dye in the reagent spreading layer is in the range from about 0.2 to 3 $g/m^2$, preferably from about 0.4 to 1.5 $g/m^2$.

Preferable hydrophilic polymers holding the indicator dispersed therein are that, when an aqueous liquid sample is supplied to the spreading layer by spotting, they are gradually dissolved in the water contained in the sample or swelled, and they can hold the indicator in a dispersed state substantially without reacting with nor fixing the indicator. The inventors have found that, by incorporating the indicator dispersed in the hydrophilic polymer into the spreading layer, the color due to the bonding between albumin being the analyte and the indicator produces relatively much in the support side (lower side) of the porous spreading layer, and the color due to the bonding between globulin or other proteins and the indicator produces relatively much in the outer surface side (upper side) portion of the porous spreading layer. Therefore, the color due to the bonding between albumin and the indicator can selectively be measured by measuring photometrically the optical density of the developed color in the element from the support side. Thus, the error caused by interference components can be decreased, and the quantitative accuracy of albumin can be raised. The hydropholic polymer may be selected from the known hydrophilic or water soluble polymers described in Ed. Kobunshi Gakkai (Polymer Soc.), "Kobunshi Zairyo Benran (Polymer Material Handbook)", Corna, Japan, 1973, "Kagaku Daijiten (Encyclopaedia Chimica)" Kyoritsu Shuppan, Japan, 1960–1963, Ed. Nakamura, "Suiyo-Sei Kobunshi (Water-Soluble Polymers)", Kagaku Kogyo, Japan, 1973, Ed. R. L. Davidson, M. Sittig, "Water-Soluble Resins 2nd Ed.", Reinhold Book Corp., 1968, Ed. J. Brandry, E. H. Immergut, "Polymer Handbook", Interscience Publishers, 1966, etc. The hydrophilic polymer includes phdrophilic cellulose dericative polymers, hydrophilic vinyl polymers and copolymers, and hydrophilic acrylate ester polymers and copolymers. The hydrophilic cellulose derivative polymer includes the hydrophilic or water-soluble cellulose derivatives described in the aforementioned "Suiyo-Sei Kobunshi (Water-Soluble Polymers)", "Water-Soluble Resins 2nd Ed.", EP 0 162 301A, etc. Preferable hydrophilic or water-soluble cellulose derivative polymers include the water soluble cellulose ethers where a part of or substantially whole hydroxyl groups are etherified by introducing lower alkyl groups having a number of carbon atoms of 1 to 3 and/or hydroxyl group-substituted lower alkyl group having a number of carbon atoms of 1 to 4. The molecular weight of the water soluble cellulose ester is usually about 8,000 to 1,000,000, preferably about 10,000 to 300,000. Suitable cellulose ester includes methyl cellulose, ethyl cellulose, hydroxyethyl cellulose, hydroxypropylmethyl cellulose and hydrosybutylmethyl cellulose, and among them, methyl cellulose and hydroxypropylmethyl cellulose are preferable. The hydrophilic vinyl polymers and copolymers include a wide range of hydrophilic or water-soluble vinyl polymers described in the aforementioned references, EP 0 119 861A, Japanese Patent KOKAI No. 115859/1985, etc. Among them, polyvinyl alcohol, polyvinyl ether and polyvinyl pyrrolidone are preferable. The hydrophilic acrylic acid or acrylate ester-containing polymers and copolymers include polyacrylic acid, poly-$\beta$-hydroxypropylacrylate, polyacrylamide and the like. Preferable hydrophilic polymers are soluble in an organic solvent such as methanol. ethanol, $\beta$-methoxyethanol, dioxane, ethyleneglycol or the like. A suitable coating amount of the hydrophilic polymer is in the range from about 3 to 30 $g/m^2$, preferably about 5 to 20 $g/m^2$.

A hydrophobic polymer may be combined with the hydrophilic polymer. By the incorporation of the hydrophobic polymer, the release rate of the indicator from the polymer can be controlled through a desired wide range. The hydrophobic polymer may be compativle to and substantcally uniformly blendable with the hydrophilic polymer, or alternatively, it may be poor in the compatibility so that phase separation occurs. The blending amount of the hydrophobic polymer is usually less than about 40 %, preferably less than about 33 %, by weight of the hydrophilic polymer. The hydrophobic polymer includes hydrophobic cellulose derivative polymers, hydrophobic vinyl polymers and copolymers, and hydrophobic acrylic acid derivative polymers and copolymers. The hydrophobic cellulose derivative polymers include hydrophobic cellulose ethers such as methyl cellulose and ethyl cellulose and hydrophobic cellulose esters such as acetyl cellulose. The hydrophobic vinyl polymers and copolymers include polyvinyl acetate and polyvinyl methyl ether. The hydrophobic acrylic acid devivative polymers and copolymers include acrylic acid ester polymers such as polymethyl acrylate, polyethyl acrylate and polybutyl acrylate and methacrylic acid ester polymers such as methacrylate lauryl ester copolymer.

The incicator is dispersed in the hydrophilic polymer, and incorporated into the spreading layer. As such a method, an aqueous solution, water-organic solvent mixture solution or organic solvent solution containing the indicator and the polymer may be applied or sprayed substantially uniformly onto the spreading layer laminated on the hydrophilic polymer binder layer according to a known method, and then dried. the above organic solvent may be selected from aliphatic alcohols such as methanol, ethanol and isopropanol, dialkylketones such as acetone and methyl ethyl ketone, dialkyl ethers such as dimethyl ether, aliphatic cyclic ethers such as tetrahydrofuran and dioxane, acetonitrile, hexane, β-methoxyethanol, ethylene glycol and the like. Instead, the spreading layer material is immersed in the solution containing the indicator and the hydrophilic polymer, and the dried or half-dried spreading layer material is laminated onto the hydrophilic polymer binder layer. In the former method, the solvent employed is preferably not dissolve the hydropholic polymer binder of the hydrophilic polymer binder layer. The indicator and the hydrophilic polymer may be uniformly suspended as well as dissolved in the above aqueous solution, water-organic solvent misture solution or organic solvent solution.

A pH buffer is incorporated into the spreading layer. The pH buffer is an organic acid or an acidic pH buffer containing an organic acid, and it can maintain the pH of the area to about 2 to 4, preferably about 2.5 to 3.5 where an aqueous liquid sample such as a biological body fluid represented by whole blood, blood plasma, blood serum, lymph, cerebrospinal fluid and urine is spotted and spreaded. The organic acid is a hydroxycarboxylic acid or a dicurboxylic acid. Examples of the hydroxycarboxylic acid are described in U.S. Pat. No. 4,333,733, Japanese Patent KOKAI Nos. 243364/1986 and 27664/1987 such as malic acid, lactic acid, citric acid and tartaric acid. Examples of the dicarboxylic acid are malonic acid, succinic acid, glutaric acid, adipic acid, pimeric acid and 3,3-dimethylglutaric acid. Among them, malic acid is preferable. Other pH buffer compositions described in The Chemical Society of Japan, "Kagaku Benran Kiso-Hen (Chemical Handbook, Fundamental Volume)", Maruzen, Tokyo, 1966, pp 1312-1320, U.S. Pat. No. 3,438,737 and the like are also usable. Two or more pH buffer may be combined. A suitable content of the pH buffer in the spreading layer is in the range from about 30 to 500 milliequivalent, preferably from about 50 to 300 milliequivalent. In the case of malic acid, a suitable content is in the range from about 2 to 35 $g/m^2$, preferably from about 3.5 to 20 $g/m^2$. The pH buffer may be incorporated together with the indicator. In this case, suitable solvent dissolves or uniformly suspends the pH buffer in addition to the indicator and the hydrophilic polymer.

A surfactant may be incorporated into the spreading layer together with the indicator, the pH buffer and the hydrophilic polymer. By incorporating the surfactant, the uniformity of the indicator and the polymer in the spreading layer is raised, and the release rate of the indicator can be controlled at the time when an aqueous liquid sample is spotted. Moreover, spreading of an aqueous liquid sample can be made uniform. The surfactant may be anionic surfactant, cationic surfactant, nonionic surfactant or ampholytic surfactant, and however, nonionic surfactant is preferable. The nonionic surfactant includes p-octylphenoxypolyethoxyethanol, p-nonylphenoxypolyethoxyethanol, polyoxyethlene oleyl ether, polyoxyethylene sorbitan monolaurate, p-nonylphenoxypolyglycidol, octylglucoside and the like. Among them, polyoxyethylene oleyl ether is preferable. The content of the nonionic surfactant in the spreading layer is usually in the range from about 20 $mg/m^2$ to about 10 $g/m^2$, preferably about 30 $mg/m^2$ to about 5 $g/m^2$. The hydrophilic polymer binder layer is water-absorptive, and the principal compoment is a hydrophilic polymer binder absorbing water to swell. This layer is also called water-absorption layer. The water-absorption layer has a function that, when the water contained in an aqueous liquid sample spotted onto the reagent spreading layer reaches the upper surface of the water-absorption layer, spreading of the aqueous liquid sample in the reagent spreading layer is improved. The polymer binder is a hydrophilic nonprotein polymer including polyacrylamide, agarose, the acrylamide copolymers such as acrylamide-N-vinylpyrrolidone copolymer disclosed in Japanese Patent KOKAI Nos. 50660/1982 and 77664/1983, the methallyl alcohol copolymers such as binary or ternary copolymers of methallyl alcohol and acrylamide or its derivative, acrylic acid or its derivative, methacrylic acid or its derivative, or N-vinyl-2-pyrrolidone. The methallyl alcohol copolymers such as acrylamide-N vinyl-2-pyrrolidonemethallyl alcohol ternary copolymer can be hardened by crosslinking. Preferable hydrophilic nonprotein polymers include acrylamide copolymers such as acrylamide-N-vinyl pyrrolidone copolymer and methallyl alcohol-containing copolymers such as acrylamide-N vinyl 2-pyrrolidone-methallyl alcohol ternary copolymer. Two or more polymer binders may be combined. A suitable coating amount of the polymer binder composing the water-absorption layer is in the range from about 1 to 100 $g/m^2$, preferably about 7 to 70 $g/m^2$.

The water-absorption layer may contain various components not affected adversely upon the ability of the indicator binding to the albumin being the analyte. For example, by incorporating a nonionic surfactant, the water contained in the aqueous liquid sample spotted is more easily absorbed by the water absorption layer substantially uniformly, and the liquid migration from the reagent spreading layer becomes repid and substantially uniform. The nonionic surfactant may be selected from mentioned previously. The water-absorption layer may also contain a pH buffer mentioned previously. A crosslinking agent (curing agent, hardening agent) may be incorporated into the water absorption layer. The crosslinking agent may be selected from various inorganic or organic crosslinking agents known in organic polymer chemical fields. for example, dimethylurea is usable as the crosslinking agent of polyvinyl alcohol, and formaldehyde is usable as the crosslinking agent of methallyl alcohol-containing copolymers, respectively. A suitable content of the crosslinking agent varies according to the coating amount of the water-absorption layer, curing degree and the like, and it is usually in the range from about 50 to 1000 $mg/m^2$, proferably about 80 to 800 $mg/m^2$. Two or more water-absorption layers may be incorporated, and in such a case, a high molecular weight pH buffer or a high molecular weight acid may be incorporated into the layer near the spreading layer. The high molecular weight acid includes known carboxyl group-containing polymers and sulfonic acid-containing polymers. In the case of incorporating two or more water-absorption layers, the layer near the support may be composed of a hydrophilic polymer not a hydrophilic nonprotein polymer, such as deionized gelatin.

As the water impermeable light transmissive support, a known support employed in an usual multilayer analytical element may be employed. Such a support is a transparent film, a sheet or a flat plate having a thickness of about 50 $\mu m$ to about 1 mm, preferably about 80 $\mu m$ to about 0.3 mm and capable of transmitting visible light (or other electromagnetic radiation) the object light having a wave length within the renge of about 200 to 900 nm. Such a support may be made polyethlene terephthalate, polycarbonate of bisphenol A, a cellulose ester (for example, cellulose diacetate, cellulose triacetate or cellulose acetate propionate), or polystyrene. A known undercoating or subbing layer or a known adhesive layer may be provided on the surface of the support in order to secure the adhesion of the support to the water-absorption layer.

In a preferable embodiment of the multilayer analytical element of the invention, the distribution ratio of the color due to albumin ($K_A$) ≧ 1.0, and the distribution ratio of the color due to globulin ($K_G$) ≦ 0.6, measured by the following method. First, various physiological saline solutions are prepared, i.e. a phosphate buffered saline solution containing 0.70 w/v % of sodium chloride of pH 7.0–7.2 at 25° C. (buffered saline solution), the buffered saline solutions containing 1.0 to 8.0 g/dl of albumin (albumin-containing saline solution) and the buffered saline solutions containing 0.5 to 6.0 g/dl of globulin (globulin containing saline solution). Each 10 μl of the above solutions is individually spotted to the multilayer analytical element, and incubated at 37° C. for 6 minutes. Immediately, the developed color is measured at 37° C. by reflection photometry using the visible light having a central wave length of about 640 nm and a half width of longer than about 10 nm from the transparent support side and the spreading layer side. $K_A$ and $K_G$ are calculated by using the following formulas.

$$K_A = (P_{SA} - P_{PS})/(S_{SA} - S_{PS})$$

$$K_G = (P_{SG} - P_{PS})/(S_{SG} - S_{PS})$$

$P_{SA}$: Optical density of albunim-containing saline solution-spotted element measured from the support side.
$P_{SG}$: Optical density of globulin containing saline solution-spotted element measured from the support side.
$P_{PS}$: Optical density of buffered saline solution spotted element measured from the support side.
$S_{SA}$: Optical density of albumin-containing saline solution spotted element measured from the spreading layer side.
$S_{SG}$: Optical density of globulin containing saline solution-spotted element measured from the spreading layer side.
$S_{PS}$: Optical density of buffered saline solution-spotted element measured from the spreading layer side.

$K_A$ ≧ 1.0 and $K_G$ ≦ 0.6 in the range of the above albunim concentration and in the range of the above globulin concentration.

In the above method of measuring the distribution ratio of the color due to albumin and the distribution ratio of the color due to globulin, a relation similar to $K_A$ ≧ 1.0 and $K_G$ ≦ 0.6 can also be obtained under the following conditions. The buffered saline solution is an aqueous solution having a ph of 6.8 to 7.4 at 25° C. and a salt concentration substantially corresponding to a saline salt solution. The pH and salt concentration of the albumin-containing saline solution and the globulin-containing saline solution are in the above range. The multilayer analytical element spotted with each 10 μl of the above solutions are incubated at a constant temparature in the range of 30° to 40° C., and the developed color is measured within 10 seconds after the incubation. The buffered saline solution may be selected from various saline salt solutions described in "Iwarami Sei-butsugaku Jiten (Iwanami Biological Dictionary) 3 Ed.", pp. 701–708, Iwanami Shoten, Tokoy, 1983, "Seikagaku (Biochemical) Handbook", pp 491–493, Maruzen, Tokyo, 1984 and the saline solution (Solutio natrii chloridi isotonica) described in the Japanese Pharmacopoeia 6th Revision to 10th Revision. Though a pH buffer component is contained in the saline salt solutions, a pH buffer composition or an aqueous pH buffer solution in the above pH range may be added to the saline salt solution. The pH buffer composition and the aqueous pH buffer solution may be selected from the pH buffer compositions described previously. Preferable saline salt solutions include the saline solution described in the Japanese Pharmacopoeia and a Ringer solution, and preferable saline salt solutions added with a pH buffer include aqueous phosphate-buffered saline solutions of pH 7.0–7.2 containing 0.70 w/v % of sodium chloride.

The analytical element of the invention can be prepared according to a known method described in the foregoing patents.

The integral multilayer analytical element of the invention is preferably cut into square pieces having a side of about 15 mm to about 30 mm or circular pieces having a similar size or the lile, and put in a slide frame disclosed in U.S. Pat. No. 4,169,751, Japanese Patent KOKAI No. 63452/1982, U.S. Pat. No. 4,387,990 and Japanese Utility Model KOKAI No. 32350/1983, U.S. Pat. Nos. 4,169,751, 4,387,990, PCT application WO 83/00391, etc. to use. While, the analytical element may be supplied in a form of a long tape packaged in a cassette or a magazine or in a form of small pieces stuck on or placed in a card having an opening.

The measurement is carried out, for example, according to the manner disclosed in the specifications of the foregoing patents. About 5 μl to about 30 μl, preferably about 8 μl to about 15 μl of an aqueous sample, such as whole blood, blood plasma, blood serum, lymph or urine, is spotted on the spreading layer, and incubated at a definite temperature in the range of about 20° to about 40° C., preferably at 37° C. ro its vicinity for 1 to 10 minutes, preferably 2 to 7 minutes. Thereafter, the color due to the albumin-acid-base indicator bond developed in the multilayer analytical element is measured from the side of the support through reflection photometry using the light having the wave length of a maximum absorption or its vicinity.

The albumin content of the sample is determined by the principle of colorimetry using a previously prepared calibration curve. When this measurement is carried out by using the chemical-analytical apparatus disclosed in U.S. Pat. Nos. 4,488,810, 4,424,191 and 4,424,191, highly accurate results can easily be obtained by a simple operation.

EXAMPLES

Example 1

The following squeous solution was coated on a colorless transparent polyethylene terephthalate (PET) film support 180 μm thick, and dried at 70° C. for 48 hours to form a crosslinked water absorption layer.

| | |
|---|---|
| Acrylamide-N-vinyl-2-pyrrolidone methallyl alcohol ternary copolymer (Monomer molar ratio; 58:38:4, Viscosity of 20 wt. % aqueous solution; 400 cp at 40° C.) | 58 g/m² |
| P-Nonylphenoxypolyglycidol | 70 mg/m² |

-continued

| | |
|---|---|
| (Containing 10 glycidol units on average) | |
| 30% aqueous formaldehyde solution | 2 g/m² |

The surface of the water-absorption layer was uniformly dampened with 30 g/m² of water, and a knitted fabric 250 μm thick was lightly pressed to laminate theron as the porous spreading layer. This knitted fabric was made of 50 deniers PET spun yarn, and previously washed and made hydrophilic.

The following mixture ethanol solution was applied onto the spreading layer, and dried to complete the integral multilayer analytical element for the quantitative analysis of albumin.

| | |
|---|---|
| Polyvinyl pyrrolidone | 8.3 g/m² |
| (Mean molecular weight: 360,000) | |
| Bromocresol Green | 690 mg/m² |
| Malic acid | 13.3 g/m² |
| Polyoxyethylene oleyl ether | 3.2 g/m² |
| (Containing 7 hydroxyethylene units on average) | |

Comparative Example 1

A comparative integral multilayer analytical element for the quantitative analysis of albumin was prepared in the same manner as Example 1, except that polyvinyl pyrrolidone was not added.

Evaluation Test 1

An aqueous 50 mmol. monopotassium dihydrogen phosphate solution containing 0.70 w/v % of sodium chloride was mixed with an aqueous 50 mmol. dipotassium monohydrogen phosphate solution containing 0.70 w/v % of sodium chloride so that the pH of the mixed solution became 7.0 at 25° C. to prepare a buffered saline solution containing 50 mmol. of phosphate and 0.70 w/v % of sodium chloride having a pH of 7.0 at 25° C. The saline solution containing 4% of human albumin and the saline solution containing 4% of human albumin and 5% of human globulin were prepared using the above buffered saline solution, respectively. Each 10 μl of these solutions was spotted on the reagent-containing spreading layer of the element of Example 1 and the element of Comparative Example 1, and incubated at 37° C. for 6 minutes. Immediately, the optical density of the reagent spreading layer was measured from the PET support side by reflection photometry using the visible light having a central wave length of 640 nm. The results are shown in Table 1.

TABLE 1

| | $D_A$ | $D_{A+G}$ | Error |
|---|---|---|---|
| Example 1 | 0.860 | 0.872 | 1.4% |
| Comparative 1 | 0.904 | 0.993 | 9.8% |

$D_A$: Optical density of albumin containing saline solution-spotted element
$D_{A+G}$: Optical density of albumin and globulin-saline containing saline solution-spotted element
Error: $[(D_{A+G} - D_A)/D_A] \times 100$ (%)

As shown in Table 1, it is clear that the error of the analytical element of the invention due to the coexisting globulin in the liquid sample was sharply decreased compared with the analytical element of Comparative Example 1 corresponding to the prior art. In the case of the analytical element of the invention, the error is about one seventh of the latter analytical element, and there is substantially no error.

Evaluation Test 2

The following saline solutions were prepared using the buffered saline solution prepared in Evaluation Test 1 as the aqueous liquid samples for measuring the distribution ratio of the developed color.

Four albumin-containing saline solutions containing 50 mmol. of phosphate, 0.70 w/v % of sodium chloride and 2.0 g/dl, 3.8 g/dl, 5.6 g/dl or 6.4 g/dl of human albumin having a pH of 7.0 at 25° C.

Five globulin containing saline solutions containing 50 mmol. of phosphate, 0.70 w/v % of sodium chloride and 1.8 g/dl, 4.2 g/dl, 5.8 g/dl, 7.2 g/dl or 9.2 g/dl of human globulin having a pH of 7.0 at 25° C.

Each 10 μl of the above ten solutions was spotted on the reagent spreading layer of the element of Example 1 and the element of Comparative Example 1, and inculated at 37° C. for 6 minutes. Immediatelly, the optical density of the reagent spreading layer was measured from the PET support side and the spreading layer side by reflection photometry using the visible light having a central wave length of 640 nm and a half width of about 20 nm. As a result, in the case of the color due to albumin, the reflection optical density of the PET support side was large, whereas, in the case of the color due to globulin, the reflection optical density of the spreading layer was large. The distribution ratio of the color due to albumin $K_A$ and the distribution ratio of the color due to globulin $K_G$ were calculated, and are summarized in Table 2.

TABLE 2

| Albumin Conc. (g/dl) | 2.0 | 3.8 | 5.6 | 6.4 | |
|---|---|---|---|---|---|
| $K_A$ | 1.8 | 1.7 | 2.0 | 1.9 | |
| Globulin Conc. (g/dl) | 1.8 | 4.2 | 5.8 | 7.2 | 9.2 |
| $K_G$ | 0.48 | 0.42 | 0.42 | 0.46 | 0.48 |

The data in Table 2 indicates that, in the case of the analytical element of the invention, the $K_A$ values representing the relectivity ot albumin are always larger than 1.0, and the $K_G$ values representing the elimination degree of the interference by globulin are always smaller than 0.6. It is clear from these data that, when the analytical element of the invention is used and the developed color is measured from the transparent support side by reflection photometry, the competitive inhibition by globulin can substantially be excluded.

Example 2

Another integral multilayer analytical element for the quantitative analysis of albumin was prepared in the same manner as Example 1, except that polyvinyl pyrrolidone was replaced by the mixture of hydroxypropyl cellulose and ethyl cellulose in a mixing ratio by weight of 3:1. The evaluation tests were carried out in a similar manner to Evaluation Test 1 and Evaluation Test 2, and similar results were obtained.

Example 3

Another integral multilayer analytical element for the quantitative analysis of albumin was prepared in the same manner as Example 1, except that the aqueous solution for forming the water absoprtion layer was replaced by the following solution and air-dried at about 23 to 26° C.

| | |
|---|---|
| Acrylamide-N-vinyl-2-phrrolidone copolymer | 45 g/m² |
| (Monomer ratio by weight; 1:1, Mean molecular | |

-continued

| | |
|---|---|
| weight; 100,000) | |
| P-Nonylphenoxypolyglycidol | 60 mg/m² |
| (Containing 10 glycidol units on average) | |

The evaluation tests were carried out in a similar manner to Evaluation Test 1 and Evaluation Test 2, and similar results were obtained.

We claim:

1. In an integral multilayer analytical element for the analysis of albumin in a sample containing interfering protein having, in this order, a porous spreading layer, at least one hydrophilic polymer binder layer, and a light-transmissive, water-impermeable support layer, wherein one surface of this spreading layer faces the support layer and the other surface of the spreading layer faces away from the support layer and the support layer contains an indicator compound capable of binding to albumin and the interfering protein to produce a color change, the improvement which comprises said spreading layer containing a pH buffer and said indicator in the spreading layer being dispersed in a hydrophilic polymer or a mixture of a hydrophilic polymer and a hydrophobic polymer, such that the color change due to albumin binding occurs substantially towards the surface of the spreading layer facing the support layer and the color change due to the interfering protein occurs substantially towards the surface facing away from the support layer.

2. A process for preparing the analytical element of claim 1 which comprises dissolving or uniformly suspending the indicator and the hydrophilic polymer in a liquid medium, incorporating the solution or the suspension into the spreading layer, and drying the spreading layer.

3. A process for preparing the analytical element of claim 1 which comprises dissolving or uniformly suspending the pH buffer and the hydrophilic polymer in a liquid medium, incorporating the solution or the suspension into the spreading layer, and drying the spreading layer.

4. The analytical element of claim 1 wherein the hydrophilic polymer of said hydrophilic polymer binder layer is a copolymer containing methallyl alcohol unit.

5. The analytical element of claim 1 wherein said indicator is an acid-base indicator dye indicating protein error.

6. The analytical element of claim 5 wherein said acid-base indicator dye is Bromocresol Green or Bromocresol Purple.

7. The analytical element of claim 1, 5, 6 or 4 of which the distribution ratio of the color due to albumin $(K_A) \geq 1.0$, and the distribution ratio of the color due to globulin $(K_G) \leq 0.6$, and $K_A$ and $K_G$ are determined by (a) preparing a phosphate buffered saline solution containing 0.70 w/v % of pH 7.0–7.2 at 25° C., samples of the buffered saline solution containing 1.0 to 8.0 g/dl of albumin and samples of the buffered saline solution containing 0.5 to 6.0 g/dl of globulin;

(b) applying 10 μl of each of the above solutions individually to the multilayer analytical element;

(c) incubating each element at 37° C. for 6 minutes;

(d) measuring the color developed at 37° C. by reflection photometry using visible light having a wave length of about 640 nm and a half width of longer than about 10 nm from the transparent support side and from the spreading layer side; and (e) calculating $K_A$ and $K_G$ From the following formulas $$K_A = (P_{SA} - P_{PS})/(S_{SA} - S_{PS})$$

$$K_G = (P_{SG} - P_{PS})/(S_{SG} - S_{PS})$$

$P_{SA}$: Optical density of albumin-containing saline solution-spotted element measured from the support side;

$P_{SG}$: Optical density of globulin-containing saline solution-spotted element measured from the support side;

$P_{PS}$: Optical density of buffered saline solution-spotted element measured from the support side;

$S_{SA}$: Optical density of albumin-containing saline solution-spotted element measured from the spreading layer side;

$S_{SG}$: Optical density of globulin-containing saline solution-spotted element measured from the spreading layer side;

$S_{PS}$: Optical density of buffered saline solution-spotted element measured form the spreading layer side.

* * * * *